United States Patent [19]
Self

[11] Patent Number: 5,641,690
[45] Date of Patent: *Jun. 24, 1997

[54] METHOD OF DETERMINING HAPTENS, USE OF METHOD AND COMPONENTS USEFUL IN METHOD

[75] Inventor: Colin Henry Self, Ponteland, United Kingdom

[73] Assignee: Cambridge Patent Developments Limited, England

[*] Notice: The term of this patent shall not extend beyond the expiration date of Pat. No. 5,468,651.

[21] Appl. No.: 560,811

[22] Filed: Nov. 20, 1995

Related U.S. Application Data

[62] Division of Ser. No. 276,766, Jul. 18, 1994, Pat. No. 5,468,651, which is a continuation of Ser. No. 465,107, filed as PCT/GB88/01033, Nov. 23, 1988, published as WO89/05433, Jun. 15, 1989, abandoned.

[30] Foreign Application Priority Data

| Nov. 28, 1987 | [GB] | United Kingdom | 8727898 |
| Jan. 30, 1988 | [GB] | United Kingdom | 8802097 |

[51] Int. Cl.$^6$ .................................................. G01N 33/53
[52] U.S. Cl. .................. 436/548; 435/7.1; 435/965; 435/971; 436/518; 436/536; 436/540; 436/822; 530/387.1; 530/387.2; 530/388.25; 530/388.9; 530/391.1; 530/391.3
[58] Field of Search .................. 435/7.1, 971; 436/518, 436/536, 537, 540, 548, 822; 530/387.1, 387.2, 388.25, 388.9, 391.1, 391.3, 810

[56] References Cited

U.S. PATENT DOCUMENTS

| 3,998,943 | 12/1976 | Ullman | 530/363 X |
| 4,185,084 | 1/1980 | Muchida et al. | 424/1 |
| 4,670,383 | 6/1987 | Baier et al. | 435/971 X |
| 4,900,661 | 2/1990 | Guesdon et al. | 435/7.92 |
| 4,956,303 | 9/1990 | Self | 436/542 |

FOREIGN PATENT DOCUMENTS

| 0139389 | 5/1985 | European Pat. Off. . |
| 0161107 | 11/1985 | European Pat. Off. . |
| 0192565 | 8/1986 | European Pat. Off. . |
| 0264219 | 4/1988 | European Pat. Off. . |
| 2161165 | 1/1986 | United Kingdom . |
| 2190490 | 11/1987 | United Kingdom . |
| 8500226 | 1/1985 | WIPO . |
| 8504422 | 10/1985 | WIPO . |

OTHER PUBLICATIONS

K.M. Gorman et al., Clin Chem, Fol. 37, No. 6, 1991 Antiidiotypic Antibodies as Alternative Labels in Competitive Immunoassays for Thyroxine.

Roitt, "Essential Immunology", Blackwell Scientific Publications, Oxford, England, p. 43, (1977).

*Primary Examiner*—Marian C. Knode
*Assistant Examiner*—Susan C. Wolski
*Attorney, Agent, or Firm*—Graham & James LLP

[57] ABSTRACT

A method is described for determining a hapten which method comprises (i) contacting the hapten with a binding partner of the hapten, whereby the hapten becomes bound to some of the binding partner, (ii) contacting the unbound binding partner with a secondary binding partner therefor, (iii) contacting the binding partner with an antibody which binds the binding partner which has bound thereto the hapten but which does not bind the binding partner which has bound thereto its secondary binding partner; and (iv) determining the amount of antibody bound to the binding partner. Kits for use in the method are also described.

60 Claims, No Drawings

METHOD OF DETERMINING HAPTENS, USE OF METHOD AND COMPONENTS USEFUL IN METHOD

This is a continuation of U.S. Ser. No. 276,766, filed Jul. 18, 1994, now U.S. Pat. No. 5,468,651, issued Nov. 21, 1995; which was a continuation of U.S. Ser. No. 465,107, filed as PCT/GB88/01033, Nov. 23, 1988, published as WO89/05433, Jun. 15, 1989, abandoned.

This invention relates to a method of determining haptens, to the use of that method and to components including kits useful in that method.

At present there are a number of commercially available methods of determining haptens. However such methods frequently suffer from the disadvantage of producing an increasing signal as the concentration of the hapten decreases. This is often inconvenient and can be a source of variablility, noise or error. Another difficultly with many commercially available methods of determining haptens is that they can be sensitive to the amounts of certain reagents employed. I believe that it would be desirable to provide a method that enables haptens to be determined in a manner that allows the determination to produce a response which increases as the concentration of the haptens increase (as opposed to the inverse ratio which often applies). It would be an added advantage if such a method could employ excess reagents such as certain antibodies, especially labelled antibodies, so that precision would not be adversely effected by small variations in the amount of such reagents employed.

Many of the preceeding advantages are offered by the systems described in European Patent Application Nos. 85901495.3, 85903019.9 and 87308829.8 in which antibodies are described which bind a complex of a small molecule and an antibody thereto but do not bind the small molecule or the antibody thereto alone. Unfortunately preparing the antibodies disclosed in those Patent Applications is believed to be frequently tedious with considerable repetitive procedures to be followed if antibodies having the desired level of specificity are to be achieved. It is believed that high backgrounds can result if specificity is sacrificed to ease of preparation. Patent Application No. PCT/GB87/00461 discloses a further class of antibodies which can bind a complex of small molecule and an antibody thereto and can bind that antibody against the small molecule but cannot bind the small molecule alone. These could be used in determination methods and can be readily produced. Unfortunately they were not said to allow the determination of haptens other than by limited methods such as, for example, by using labelled haptens in competitive assays.

I believe that it would be desirable to provide a method of determining haptens which employs antibodies which can be produced relatively easily but still offers advantages as set forth hereinbefore and can be used in a variety of manners. Such a method has now been discovered.

The present invention provides a method of determining a hapten which method comprises (i) contacting the hapten with a binding partner of the hapten, whereby the hapten becomes bound to some of the binding partner, (ii) contactng the unbound binding partner with a secondary binding partner therefore, (iii) contacting the binding partner with an antibody which binds the binding partner which has bound thereto the hapten but which does not bind the binding partner which has bound thereto its secondary binding partner; and (iv) determining the amount of antibody bound to the binding partner.

The antibody referrd to in (iii) and (iv) above will often be referred to as the "selective antibody" hereinafter. The selective antibody may be polyclonal although I prefer to employ a monoclonal selective antibody.

When the term "antibody" is used it should be realized that the antibody can be the whole immunoglobulin or fragments thereof which containing the binding site (such as Fab, F(ab$^1$)$_2$, Fv). The antibody may also be an aggregate or hybrid but this is usually less preferable. Using a fragment as the binding partner of the hapten (such as a Fab fragment) can be particularly useful.

When used herein the term "hapten" has the normal meaning of a small molecule which is not itself immonogenic. The skilled art worker will appreciate that low molecular weight materials such as small molecules for determination by this invention are normally non-immunogenic but that antibodies against these haptens can be obtained by immunizing an animal with a conjugate of the non-immunogenic molecule (or sometimes a very close analogue) and an immunogenic material (such as bovine serum albumin or an equivalent agent).

It will be understood that haptens are small molecules. Such haptens aptly have a molecular weight of for example 100 to 1500, more suitably from 120 to 1200 and favorably from 200 to 1000. Haptens with molecular weights of less than 1000 are often of particular interest for this invention. European Patent Application No. 85901495.3 and 85903019.9 and Patent Aplication No. PCT/GB87/00461 may be consulted for the types of haptens which are most suitable for determination by the method of this invention. European Patent Application No. 87308829.8 may similarly be consulted.

Haptens of particular interest for determination may be selected from amongst groups such as medicaments, drugs of abuse, metabolites, industrial chemicals (such as pollutants and agrochemicals), toxins and the like.

In order to facilitate the determination of the amount of selective antibody bound to the binding partner it is apt that either the selective antibody or the binding partner is immobilized. Precipitation of the complex including the binding partner and the selective antibody is also envisaged but this is thought to be less apt than employing immobilization of the selective antibody or the binding partner. The immobilization employed may be any suitable method but in general attachment to a solid surface, for example to the surface of a plate, tube, dip-stick, capilliary, paper, gel or the like is favoured.

The secondary binding partner for the haptens binding partner may be any which will bind to that binding partner and which once bound will prevent significant binding of the antibody thereto. Generally the secondary binding partner will be an analogue or derivative of the hapten. Most suitably the secondary binding partner will be a moiety which is sufficiently large to prevent binding of the antibody by steric effects. I believe that a particularly favoured class of secondary binding partners are large binding partners and that these are preferably large derivatives of the hapten, for example conjugates of the hapten with a large molecule or of a close analogue of the hapten with a large molecule. Such large molecules will most suitably have a molecule weight of greater than 5000 and will preferably be macromolecules, for example proteins. Typically these macromolecules will have molecular weights greater than 10000, more aptly greater than 20000 and preferably greater than 40000. I believe conventional macromolecules such as albumin (for example bovine serum albumin) are suitable for conjugation to the hapten.

If a conjugate of a hapten (or a close analogue) and large molecule is used to raise the binding partner, then that conjugate is often a particularly suitable secondary binding partner. It is often advantageous that the conjugate or secondary binding partner so employed are highly water soluble (although those conjugates of lower solubility can be employed). The skilled art worker will be aware that such conjugates are readily available and may be obtained by many conventional methods of conjugation.

The secondary binding partner can advantageously be an antibody against the binding partner of the hapten, for example against the hapten binding site, for example an anti-idiotypic antibody. It can be particularly advantageous to use a fragment of the anti-idiotypic antibody as previously indicated.

The skilled art worker will appreciate that the binding partners will usually be selected to bind with as high an affinity as conveniently obtainable but that the affinity of the selective antibody for the secondary binding partner binding partner complex should be as low as conventiently obtainable.

The determination may employ a label if desired. If this is so it will not be on an immobilized member of the selective antibody binding partner pair.

In some aspects of the invention a label will not be required; for example, where association of the hapten, primary partner and selective antibody is measured directly, for example by electrical, optical or other means for example by modification of a surface such as a diffraction grating or the like in which reflectance properties change on deposition.

The binding partner for the hapten may be any suitable binding material such as a specific binding protein or antibody but I believe best results are obtained when a monoclonal antibody is employed as the binding partner for the hapten.

From the foregoing it will be clear that in a favored aspect the present invention provides a method of determining a hapten which method comprises (i) contacting the hapten with a labelled monoclonal antibody therefor whereby the hapten becomes bound to some of the labelled monoclonal antibody, (ii) contacting the unbound labelled monoclonal antibody with a large binding partner therefor; (iii) contacting the labelled monoclonal antibody with an immobilized antibody which binds the labelled monoclonal antibody which has bound thereto the hapten but which does not bind the labelled monoclonal antibody which has bound thereto its large binding partner; and (iv) determining the amount of antibody bound to the labelled monoclonal antibody. The determination will be effected using the label on the labelled monoclonal antibody. Normally the thus immobilized label will be assayed after separation of the liquid phase and washing the solid.

From the foregoing it will also be clear that in a particularly favoured aspect the present invention provides a method of determining a hapten which method comprises (i) contacting the hapten with an immobilized monoclonal antibody therefore whereby the hapten becomes bound to some of the monoclonal antibody,(ii) contacting the unbound immobilized monoclonal antibody with a large binding partner therefore, (iii) contacting the immobilized monoclonal antibody with a labelled antibody which binds the immobilized monoclonal antibody which has bound thereto the hapten but which does not bind the immobilized monoclonal antibody which has bound thereto its large binding partner; and (iv) determining the amount of labelled antibody which has become bound to the immobilized monoclonal antibody. The determination will be effected using the label on the labelled monoclonal antibody and normally that which has become bound to the solid. Normally the thus immobilized label will be assayed after separation of the liquid phase and washing the solid.

The amount of binding partner for the hapten (generally a monoclonal antibody) employed will normally be such that it is not saturated on exposure to the hapten; an excess is advantageously present with the resulting benefit that the assay is not unduly effected by the size of that excess within reasonable limits. This is easily achieveable by using an excess of binding partner over the likely amount of sample to be tested. In practice this will provide the skilled worker with little difficulty as the likely concentration of hapten in a sample is generally known (or can be estimated) within broad limits and ranging experiments can be carried out if necessary. Similarly an excess of secondary binding partner will also normally be employed and this can be estimated by the skilled worker without difficulty although ranging experiments can be carried out if necessary.

The source of the hapten for diagnostic tests may be blood, serum, saliva, urine or other source suspected of containing the haptens. Other sources such as food samples, industrial samples, laboratory samples are also envisaged. The source may be purified or concentrated before use if desired. Thus the hapten being introduced into the test method may be in its original medium or in a subsequent medium. Such sample handling is conventional and does not form part of the present invention.

The antibody which binds thereto the binding partner of the hapten which actually has bound thereto hapten (ie the selective antibody) can have varying degrees of affinity for the binding partner of the hapten which has not bound thereto hapten (eg. the primary antibody). In the case where the binding of the antibody to the binding partner of the hapten which has bound thereto hapten is high compared to the binding partner of the hapten which has not bound hapten, then the secondary binding partner and the selective antibody may be added simultaneously. When the ratio is lower, as is generally the case, it will be advantageous to add the secondary binding partner first and then subsequently add the selective antibody.

Since I believe that it is easier to produce antibodies with some residual binding of the free binding partner for the hapten I consequently prefer to use a method of determination in which the selective antibody is introduced after the secondary binding partner has been introduced.

Generally the incubation periods used in this invention are from about 1 minute to 2 hours, more usually from 2 minutes to 100 minutes, for example 10 to 60 minutes.

The method of determining the amount of antibody bound to the hapten's binding partner may be any method chosen to suit the users' convenience. Generally one of the antibody and binding partner will be labelled with a signal generating means. This means may be present in situ throughout the method or may be added subsequently, for example by a "Sandwich" technique such as usng another antibody which is itself labelled to bind to antibody or binding partner. However, I prefer to use a label which has been present on the antibody or binding partner throughout the method.

The method of determining the amount of antibody bound to the hapten's binding partner may be indirect (for example by determining the amount not bound and determining the amount bound by difference) although it is preferred to determine the amount of antibody bound to the hapten's binding partner directly.

The determination will aptly employ measurement of a label present on the selective antibody or on the hapten's binding partner. The label employed may be any convenient label such as a radiolabel (for example $C^{14}$ or $H^3$) or a luminescent label (for example a bioluminescent, fluorescent or chemiluminescent label) or enzyme labels (such as a phosphatase, peroxidase, β-galactosidase or the like or coenzyme label. The label may be used to produce an amperometric change if desired. European Patent Application Nos. 85901495.3, 85903019.9 and Patent Application No. PCT/GB87/00461 may be consulted for suitable labels and their measurement. The solid surface I prefer to employ is a microtitre well. The label I believe most apt is an enzyme label of which I prefer an alkaline phosphatase. This may be determined in convenient manner, for example by dephosphorylation of p-nitrophenylphosphate or by dephosphorylation of NADP or NADPH which then starts an amplification cycle. The choice of such assay method is wide and the skilled art workers may chose such a method for their own convenience.

The various stages of the method of this invention will take place under conditions conventionally used in immunoassays. Thus for example the temperature will be non-extreme, for example 4°–40° C. and most suitably ambient, the aqueous solutions employed may contain conventional buffers and isotonicity adjusting agents as required so that the solutions are at non extreme pH's and tonicities.

Particularly suitable selective antibodies for use in this invention can be raised as described in Patent Application No. PCT/GB87/00461 because of their easier availablility.

Any convenient method of labelling of the selective antibody may be employed but I prefer to use the method of Voller or those of Ishikawa et al (J. Immunoassay 1983, 4, 209–327) especially those employing the use of hereto bifunctional cross linking agents.

It can be advantageous to use as secondary binding partner the material which has been used to raise the antibody (normally the monoclonal antibody) against the hapten (for example hapten linked to BSA can be used to raise antihapten monoclonal antibody and can be the secondary binding partner).

The selective antibodies may be raised by the methods of patent applications refered to hereinbefore and also Patent Application No. PCT/GB87/00461. In some cases, especially where the hapten is naturally present in the animal or cell, it may be sufficient to immunize with hapten binding partner although I prefer to use hapten and hapten binding partner. The hapten and binding partner may first be formed into a complex if desired which complex may be covalently bound if required.

The method of this invention offers the advantage of not needing a step to remove hapten bound binding partner from hapten unbound binding partner. Similarly this invention does not require removal of the binding partner bound by hapten prior to the determination of the amount of selective antibody bound to the binding partner. Similarly this invention offers the advantage of not requiring special dedicated equipment if this is not convenient.

In a preferred aspect this invention provides a method of determining a hapten which method comprises (a) absorbing a monoclonal antibody to the hapten onto a solid surface, (b) contacting the thus immobilized monoclonal antibody with a solution of the hapten whereby hapten becomes bound to some of the monoclonal antibody and then with a solution of a large derivative of the hapten whereby the remaining monoclonal becomes bound; (c) contacting the thus bound immobilized monoclonal antibody with a labelled antibody which binds to the hapten bound monoclonal antibody but not the large derivative of the hapten bound monoclonal antibody; (d) separate the immobilized labelled antibody from the non-immobilized labelled antibody; and (e) determine the amount of label which has become immobilized.

The present invention also provides a kit for determination of a hapten which comprises a binding partner for the hapten, a secondary binding partner for the hapten binding partner, and a selective antibody.

Most aptly the binding partner is an immobilized monoclonal antibody. Most aptly the secondary binding partner is a large derivative of the hapten. Most aptly the selective antibody is a labelled monoclonal antibody.

Favorably the kit may also comprise reagents for the binding of the selective antibody.

Selective antibodies can be chosen by obtaining antibodies by the methods hereinbefore described and screening the cohort of antibodies produced for the desired activity.

A method of obtaining selective antibody is based on a method for determining whether the combination of the antibody under test with the primary binding partner has taken place. Selective antibody is that antibody which is found to combine with the primary binding partner in the presence of hapten but not if the primary binding partner has bound secondary binding partner. Any convenient method may be employed but I prefer to use one of the following methods. In such methods the secondary binding partner employed is often the conjugate used to raise the primary binding partner.

The antibody under test is bound to a solid surface (for example by absorption onto the surface or onto an antibody already on the surface). To this is added a primary binding partner which has been exposed to either hapten or secondary binding partner. The degree of association between the labelled antibody and the surface is determined. Those test antibodies which give rise to a higher level of binding in the presence of hapten than in the presence of secondary binding partner are chosen as selective antibodies.

The higher the level of this binding the better the selective antibody is. Normally a ten fold increase is very readily available and a 100 fold increase readily obtainable and even higher ratios obtainable with relative ease.

Alternatively a primary binding partner is bound to a solid surface. Either hapten or secondary binding partner is added. The test antibody is added and the amount of test antibody bound to the solid surface is then determined. Those test antibodies which have a higher level of binding in the presence of hapten than in the presenceof secondary binding partner are chosen as selective antibodies. The binding may be determined by employing a further labelled antibody.

Those selective antibodies which exhibit a high level of binding to the primary binding partner in the absence of hapten are generally employed sequentially in the method of this invention. If the binding is less high a simultaneous system may be used but this is not generally so easily achievable.

When a selective antibody has been obtained the above methods may be adapted to screen for suitable alternative secondary binding partners.

Selection of an antibody for use as an anti-idotypic antibody secondary binding partner in the method of this invention may use one of the many methods available for the demonstration of anti-idiotypic antibodies. The majority of these involve the demonstration of the competitive binding of the antibody with hapten for a primary receptor such as the primary binding partner described herein and such as an antibody. An example of demonstration that an antibody is as anti-idiotypic antibody for a monoclonal antibody against a hapten is as follows:

i. Surface bound monoclonal antibody is exposed to the antibody being tested.
ii. Labelled hapten to which the monoclonal antibody is specific is added to the exposed antibody as well as a duplicate preparation of the monoclonal which has not been exposed to the test antibody.
iii. Unbound labelled hapten is washed away.
iv. The amount of a label associated with and without the test antibody is measured.
v. When there is a significant reduction in the amount of label associated after the addition of test antibody (such as a 50% reduction or such greater percentage as may be achieved) then the antibody is considered as anti-idiotypic antibody.

This antibody may then be tested for its usefulness as a secondary binding partner. this involves determining whether on binding the primary binding partner the anti-idiotypic antibody inhibits the further binding of the selective antibody. Again there are many ways of carrying out this determination such as:

i. Surface bound monoclonal antibody (primary binding partner) is exposed to the anti-idiotypic antibody.
ii. Labelled selective antibody is then added to this and a duplicate preparation of the primary binding partner which has not been exposed to the anti-idiotypic antibody.
iii. Unbound labelled antibody is washed away.
iv. The amount of label associated with and without the anti-idiotypic antibody is then measured.
v. Where the anti-idiotypic antibody results in a signicant reduction of labelled associated with the primary binding partner then it is considered to be useful as a secondary binding partner in the method of this invention. A 50% reduction in the label measured may indicate a useful secondary binding partner but in general this figure should be as great as can be achieved and reductions of greater than 90% should be aimed for, and reduction of greater than 98% would be particularly useful. Other secondary binding partners may be selected in an analogous manner.

EXAMPLE 1

A murine monoclonal antibody is raised against oestradiol by conventional procedure employing as immunogen beta-estradiol 6-(O-carboxy-methyl) omime:BSA (Sigma Chemical Company Ltd cat number E5630).

Employing standard procedures monoclonal antibodies are then raised against lots of 100 µg of the anit-estradiol monoclonal antibody mixed with 200 µg estradiol. The hybridoma clones are screened for production of the required (SelAb) monoclonal antibody as follows:

Microtitre plates (Nunc Immunoplate 1 code 4-39454) are taken and the wells coated each with 100 µl of 50 mM bicabonate buffer pH 9.6 containing 1 µg of anti-mouse IgG antibody (Sigma cat no. M 8642) by leaving them overnight at room temperature. The solutions are removed and the wells filled with 0.2% casein in the same buffer and left for one hour at room temperature. They are then washed four times with 50 mM Tris pH 7.4 containing 0.02% Tween 20 (TT). Quadruplicate wells then receive 100 µl each of the same hybridoma culture fluid to be tested. They are incubated for 2 hours at room temperature 10 µl of a solution of 2 ug mouse is then mixed into each well and a further 30 minute incubation is carried out. The wells are then washed four times with TT.

A conjugate of the anti-estradiol monoclonal antibody is then made with alkaline phosphatase employing 1.5 mg of the monoclonal antibody and 5 mg of alkaline phosphatase according to the method of Voller A, .E. Bidwell and Ann Barlett, Bull. World Health Organ., 55 (1976). A dilution of 1:200 is made of this. To 40 ml of this is added 100 ug of beta-estradiol 6-(O-carboxy-methyl)oxime:BSA (solution I) and to another 40 ml the same amount of BSA (Solution II). Each quadruplicate group of wells are taken and duplicates receive 100 µl of solution I. The remaining duplicate pair receive 100 µl of solution II. The wells are then incubated for a further hour at room temperature. The solutions are then discarded and the wells washed four times with TT. Each well then receives 100 µl of 10 mM para-nitrophenyl phosphate in 50 mM bicarbonate buffer pH 10.3 and containing 3.3 mM MgCl2. The alkaline phosphatase activity is then recorded at 405 nm.

The hybridoma clones are selected for those which produce culture fluid providing the following result in the above screen: duplicated wells containing solution I—low alkaline phosphatase activity; duplicate wells containing solution II—high alkaline phosphatase activity.

The clones are purified free of contaminating clones and used to raise ascites by conventional techniques. The monoclonal antibody thus obtained is purified by means of Protein A fractionation. It is then conjugated to alkaline phosphatase as above (giving 'SelAb-Conj'). This conjugate is used in an assay for oestradiol as follows:

Microtitre plate wells are coated by the addition into each of 100 µl of 50 mM bicarbonate buffer pH 9.6 containing 1 µg of the anti-oestradiol monoclonal antibody. They are left overnight at room temperature. The wells are then glazed with 100 µl of 0.2% casein in the same buffer and left for a further hour at room temperature. They are then washed four times with TT. A serial 1:2 dilution of the oestradiol:BSA conjugate is then made in phosphate buffered saline starting with a concentration of 1 µg/ml. 100 µl of each of these are added to individual wells in duplicate and incubated for one hour at room temperature and a duplicate pair of wells receive buffer alone. The solutions are discarded and the wells are washed four times with TT. 100 µl of a 1:400 dilution of the SelAb-Conj preparation is mixed into each well and the wells incubated at room temperature for a further one hour. The solutions are then discarded and the wells washed four times with TT. 100 µl of 10 mM para-nitrophenyl phosphate in 50 mM bicarbonate pH 10.3 and containing 3.3 mM $MgCl_2$ is then added to each well and the alkaline phosphatase activity followed at 402 nm. A graph of oestradiol concentraton against phosphatase activity is then drawn which shows the power of added oestradiol-conjugate to inhibit binding of the primary and secondary antibodies. The lowest concentration of the conjugate which gives more than 90% inhibition is identified and used in the following determination.

The microtitre plates are coated with anti-estradiol monoclonal antibody, glazed and washed as in the preceding paragraph. 1:2 serial dilutions of estradiol are made from 1 µg/ml in 50 mM Tris pH 7.4. 100 µl of each of these are added to duplicate wells and the wells incubated for one hour at room temperature. 10 µl of a solution of the estrogen-conjugate at ten fold higher concentration than identified above is then mixed into each well. The wells are incubated for a further hour at room temperature. The solutions are discarded and the wells washed four times with TT. 100 µl of the SelAb-Conj is then added to each well and incubated for a further hour at room temperature. The solution is then discarded and the wells washed four times with TT. Each well then receive 100 µl of 10 mM para-nitrophenol phosphate in 50 mM bicarbonate pH 10.3 and containing 3.3 mM $MgCl_2$ and the alkaline phosphate activity followed at 402 nm. Thus a standard curve of oestradiol concentration against phosphatase activity is obtained.

Uknown samples are determined by adding them to the assay in place of the estradiol serial dilutions in the above protocol. The degree of phosphatase activity being finally found in the wells which had received the unknowns is then related to the standard curve to concentration of oestradiol in these unknown samples.

EXAMPLE 2

Example 1 is repeated but the immunization regime for producing the secondary (SelAb) monoclonal antibody is via intrasplenic immunization with 100 µg of the anti-oestradiol monoclonal antibody mixed with 200 µg of oestradiol. The first antibody coated to the microtitre plate is anti-mouse IgM antibody instead of anti-mouse IgG and also the 2 hour incubation 2 µg of mouse IgM is added in place of IgG.

EXAMPLE 3

Example 1 is repeated but the secondary antibody is polyclonal antibody produced by conventional immunization of a rabbit. The antibody is similarly purified with protein A prior to conjugation with alkaline phosphatase.

EXAMPLE 4

Example 1 is repeated with hydrocortisone in place of estradiol. Hydrocortisone 3-(O-carboxy-methyl) oxime:BSA conjugate is employed to raise the anti-hydrocortisone antibody and also subsequently in the inhibition steps.

EXAMPLE 5

Example 2 is repeated with hydrocortisone.

EXAMPLE 6

Example 3 is repeated with hydrocortisone.

EXAMPLE 7

Example 1 is repeated with progesterone in place of oestradiol. Progesterone 3-(O-Carboxymethyl)-Oxime:BSA conjugate is employed to raise the anti-progesterone monoclonal antibody and also subsequently in the inhibition steps.

EXAMPLE 8

Example 2 is repeated with progesterone.

EXAMPLE 9

A murine monoclonal antibody is obtained by conventional means against theophylline.

Mice are then immunized with the intact monoclonal antibody by multiple intra-peritoneal injections, their spleens are taken and IgG class monoclonal antibodies against the monoclonal antibody are raised. These are screened for anti-idiotypic activity as follows:

Nunc microtitre plates are coated per well with 100 µl of 50 mM bicarbonate buffer pH 9.6 containing 1 µg anti-mouse IgG antibody by overnight incubation at room temperature. The solutions are removed and the wells glazed with 200 µl per well of 0.2% casein in the same buffer for one hour at room temperature. The solutions are removed and the wells washed four times with 50 mM Tris pH 7.4. Quadruplicate wells then each receive 1 µg of an antibody to be tested in 100 µl Tris pH 7.4. They are incubated for two hours at room temperature. The wells are then washed four times with 50 mM Tris 7.4 containing 0.02% Tween 20 (TT). A conjugate of the anti-theophylline monoclonal antibody is then made with alkaline phosphatase according to the method of Voller A, E. Bidwell and Ann Barlett, Bull. World Health Organ., 53, 55 (1976). A dilution of 1:500 is made of this. Two 200 µl alliquots are taken and 50 µl of a 1 mg/ml solution of theophylline in 50 mM Tris pH 7.4 added to one while buffer alone is added to the other. Two of the quadruplicate wells then receive 100 µl of the theophylline containing solution while the other duplicate pair receive the solution without theophylline. The solutions are incubated for a further hour at room temperature. The wells are then washed four times with TT and each well given 100 µl of 10 mM para-nitrophenol phosphate in 50 mM bicarbonate buffer pH 10.3. Their phosphatase content is assessed by the rate of change of optical density at 405 nm. Screened antibodies in which the addition of theophylline very significantly reduces the amount of phophatase conjugate bound (such as a reading of 2.0 optical density units without theophylline with 0.7 optical density units with theophylline) are considered anti-idiotypic antibodies of use in the following system.

Another group of mice are immunized intro-splenically with one immunization each consisting of 100 µg of the anti-theophylline monoclonal antibody mixed with an equal quantity of theophylline in 100 µl 50 mM Tris pH 7.4. Over the next four days the mice receive three further injections of 100 g of theophylline introperitoneally.

On the fourth day their spleens are removed and hybridomas made by conventional procedure with myeloma cell line NSO. The hybridomas are screened for the required (Selab) antibody as follows:

Microtitre plates are taken and the wells coated each with 100 µl of 50 mM bicarbonate buffer pH 9.6 containing 1 µg of anti-mouse IgM antibody by leaving them overnight at room temperature. The solutions are removed and the wells filled with 0.2% casein in the same buffer and left for one hour at room temperature. They are then washed our times with TT. Quadruplicate wells then receive 100 µl each of the same hybridoma culture fluid to be tested. They are incubated for 2 hours at room temperature 100 µl of a solution of 2 µg mouse IgM is then mixed into each well and a further 30 minute incubation carried out. The wells are then washed four times with TT.

Two 200 µl aliquots of a 1:500 dilution of the anti-theophylline monoclonal antibody—alkaline phosphatase conjugate in 50 mM Tris pH 7.4 buffer containing 0.1% bovine serum albumin (TBSA) are taken. To one is added 50 µl of the buffer containing 100 µg theophylline and to the other buffer alone. The solutions are mixed and incubated for ten minutes at room temperature. To each is then added 50 µl of TBSA containing 10 µg of a selected anti-idiotypic antibody. The solutions are then incubated for a further ten minutes at room temperature. 100 µl of each is then added in duplicate to the microtiter wells which have been exposed to the antibody to be tested. A further incubation of half an hour is made at room temperature. The solutions are then discarded and the wells washed four times with TT. Each well then receives 100 µl of 10 mM para-nitrophenyl phosphate in 50 mM bicarbonate buffer pH 10.3 and containing 3.3 mM $MgCl_2$. The alkaline phosphatase activity is then determined by the optical density change at 405 nm. Where the optical density change with those duplicates which received the addition of theophylline is significantly larger than those which did not (i.e. such as 2.0 OD to 1.0 OD units) the antibody tested is considered to be a selective antibody and the hybridoma from which it derived purified free of contaminating clones and used to raise ascites by conventional techniques. The monoclonal antibody thus obtained is purified by means of Protein A fractionarian. It is then conjugated to alkaline phosphatase as above (giving 'SelAb-Conj'). This conjugate is used in an assay for theophylline as follows:

Microtitre plate wells are coated by the addition into each of 100 μl of 50 mM bicarbonate buffer pH 9.6 containing 1 μg of the anti-theophylline monoclonal antibody. They are left overnight at room temperature. The wells are then glazed with 100 μl of 8.2% casein in the same buffer and left for a further hour at room temperature. They are then washed four times with TT.

A serial 1:2 dilution of the anti-idiotypic antibody is then made in phosphate buffered saline starting with a concentration of 1 μg/ml. 100 μl of each of these are added to individual wells in duplicate and incubated for one hour at room temperature and a duplicate pair of wells receive buffer alone. The solutions are discarded and the wells are washed four times with TT. 100 μl of a 1:400 dilution of the SelAb-Conj preparation is mixed into each well and the wells incubated at room temperature for a further one hour. The solutions are then discarded and the wells washed four times with TT. 100 μl of 10 mM para-nitrophenyl phosphate in 50 mM bicarbonate ph 10.3 and containing 3.3 mM MgCl$_2$ is then added to each well and the alkaline phosphatase activity followed at 402 nm. A graph of theophylline concentration against phosphatase activity is then drawn which shows the power of added anti-idiotypic antibody to inhibit binding between the primary and secondary antibodies. The lowest concentration of the anti-idiotypic antibody which gives more than inhibition is identified and used in the following determination.

The microtitre plates are coated with anti-theophylline monoclonal antibody, glazed and washed as in the preceding paragraph. 1:2 serial dilutions of theophylline are made from 1 μg/ml in 50 mM Tris pH 7.4. 100 μl of each of these are added to duplicate wells and the wells incubated for one hour at room temperature. 10 μl of a solution of the anti-idiotypic antibody at ten fold higher concentration than identified above is then mixed into each well. The wells are incubated for a further hour at room temperature. The solutions are discarded and the wells washed four times with TT. 100 μl of the SelAb-Conj is then added to each well and incubated for a further hour at room temperature. The solution is then discarded and the wells washed four times with TT. Each well then receive 100 μl of 10 mM para-nitrophenol phosphate in 50 mM bicarbonate pH 10.3 and containing 3.3 mM MgCl$_2$ and the alkaline phosphatase activity followed at 405 nm. Thus a standard curve of theophylline concentration against phosphatase activity is obtained.

Unknown samples are determined by adding them to the assay in place of the theophylline serial dilutions in the above protocol. The degree of phosphatase activity being finally found in the wells which had received the unknowns is then related to the standard curve to concentration of theophylline in these unknown samples.

EXAMPLE 10

A monoclonal antibody is obtained against theophylline and a portion labelled with alkaline phosphatase. A monoclonal anti-idiotypic antibody is raised against the anti theophylline monoclonal antibody. A selective monoclonal antibody is raised against the anti theophylline monoclonal antibody theophylline complex. An assay for theophylline is then conducted by means of binding selective monoclonal antibody onto solid surfaces and exposing these to labelled anti-theophylline antibody exposed to a range of theophylline standard preparations or sample to be determined and the anti idiotypic antibody. The amount of alkaline phosphatase bound specifically to the surfaces is than determined and to concentration of theophylline in the sample calculated.

EXAMPLE 11

The procedure of Example 10 was employed with gentamycin in place of theophylline.

EXAMPLE 12

The procedure of Example 10 was repeated except that the monoclonal antibody against theophylline was fragmented and Fab fragment then labelled wth alkaline phosphatase and used in the determination.

EXAMPLE 13

Preparation and use of a selective antibody against tetrahydrocanibol.

By methods analogous to those described in European Patent No. 0264219: (1) a monoclonal antibody is obtained against tetrahydrocannibal (THC); (2) it is affinity labelled with THC derivative as described to form a delta-8-THC conjugate; (3) a monoclonal antibody is prepared against this conjugate. Although this antibody will bind a complex of the anti-THC monoclonal antibody and THC it also binds the anti-THC antibody on its own to a not insignificant extent so that high backgrounds result if it is used in the assays described in European Patent No. 0264219; however it may be employed effectively for the determination of THC by the method of this present invention as a selective antibody. It is employed as in Example 1 of the present specification with the following changes: the hapten to be determined is THC; the primary binding partner is the anti-THC monoclonal antibody; the selective antibody is as made as described above; the secondary binding partner is a conjugate of 11 carboxymethyloxime derivative of of delta-9-THC and bovine serum albumin prepared in conventional manner.

I claim:

1. A method of determining a hapten which method comprises (i) contacting the hapten with a primary binding partner of the hapten, whereby the hapten becomes bound to some of the primary binding partner, (ii) contacting unbound primary binding partner with a secondary binding partner therefor, (iii) contacting the primary binding partner with a selective antibody which binds the primary binding partner which has bound thereto the hapten but which does not bind the primary binding partner which has bound thereto its secondary binding partner; and (iv) determining the amount of selective antibody bound to the primary binding partner.

2. A method according to claim 1 wherein the hapten has a molecular weight of less than 1000.

3. A method according to claim 1 wherein the selective antibody is a monoclonal antibody.

4. A method according to claim 3 wherein the secondary binding partner is a conjugate of the hapten or hapten analog and a macromolecule.

5. A method according to claim 1 wherein the primary binding partner is an antibody.

6. A method according to claim 5 wherein the primary binding partner is a monoclonal antibody.

7. A method according to claim 6 wherein a conjugate of the hapten or hapten analogue and macromolecule was used to raise the primary binding partner.

8. A method according to claim 1 wherein the secondary binding partner is an antibody which binds the primary binding partner.

9. A method according to claim 1 wherein either the primary binding partner or the selective antibody is immobilized.

10. A method according to claim 1 wherein either the primary binding partner or the selective antibody is labelled.

11. A method according to claim 9 wherein whichever of the primary binding partner or selective antibody which is not immobilized is labelled.

12. A method according to claim 2 which comprises (i) contacting the hapten with a labelled monoclonal antibody therefor whereby the hapten becomes bound to some of the labelled monoclonal antibody, (ii) contacting the unbound labelled monoclonal antibody with a binding partner therefor having a molecular weight greater than 5000, (iii) contacting the labelled monoclonal antibody with an immobilized antibody which binds the labelled monoclonal antibody which has bound thereto the hapten but which does not bind the labelled monoclonal antibody which has bound thereto said binding partner; and (iv) determining the amount of antibody bound to the labelled monoclonal antibody.

13. A method according to claim 2 which comprises (i) contacting the hapten with an immobilized monoclonal antibody therefor whereby the hapten becomes bound to some of the monoclonal antibody, (ii) contacting the unbound immobilized monoclonal antibody with a binding partner therefor having a molecular weight greater than 5000, (iii) contacting the immobilized monoclonal antibody with a labelled antibody which binds the immobilized monoclonal antibody which has bound thereto the hapten but which does not bind the immobilized monoclonal antibody which has bound thereto said binding partner and (iv) determining the amount of labelled antibody which has become bound to the immobilized monoclonal antibody.

14. A kit for the determination of a hapten by a method claim 1 which comprises a primary binding partner for the hapten, a secondary binding partner for the primary binding partner and a selective antibody which binds the primary binding partner which has bound thereto the hapten but which does not bind the primary binding partner which has bound thereto its secondary binding partner.

15. A method of determining a hapten which method comprises (i) contacting the hapten with an excess of a first binding partner of the hapten, whereby the hapten becomes bound to some of the first binding partner, (ii) contacting the unbound first binding partner with a secondary binding partner therefore, (iii) contacting the first binding partner with a selective antibody which binds the first binding partner which has bound thereto the hapten but which does not significantly bind the first binding partner which has bound thereto its secondary binding partner; and (iv) determining the amount of selective antibody bound to the first binding partner.

16. A method according to claim 15 wherein the hapten has a molecular weight of less than 1000, the selective antibody is a monoclonal antibody and the first binding partner is a monoclonal antibody.

17. A method according to claim 16 wherein said secondary binding partner is a conjugate of the hapten or hapten analogue and a macromolecule and has a molecular weight greater than 5000.

18. A method according to claim 16 wherein said secondary binding partner is an antibody which binds the first binding partner.

19. A method according to claim 18 wherein the secondary binding partner is a monoclonal anti-idiotypic antibody.

20. A method according to claim 12 wherein the binding partner of molecular weight greater than 5000 is an antibody.

21. A method according to claim 13 wherein the binding partner of molecular weight greater than 5000 is an antibody thereto.

22. A method according to claim 20 wherein the antibody is an anti-idiotypic antibody.

23. A method according to claim 21 wherein the antibody is an anti-idiotypic antibody.

24. A method according to claim 22 wherein the anti-idiotypic antibody is an antibody fragment.

25. A method according to claim 23 wherein the anti-idiotypic antibody is an antibody fragment.

26. A method according to claim 16 wherein the selective antibody is labelled.

27. A kit for the determination of a hapten by a method of claim 15 which comprises a primary binding partner for the hapten, a secondary binding partner for the primary binding partner and a selective antibody which binds the primary binding partner which has bound thereto the hapten but which does not bind the primary binding partner which has bound thereto its secondary binding partner.

28. A method according to claim 1 wherein the secondary binding partner is added first and the selective antibody is added subsequently.

29. A method according to claim 2 wherein the secondary binding partner is added first and the selective antibody is added subsequently.

30. A method according to claim 15 wherein the secondary binding partner is added first and the selective antibody is added subsequently.

31. A method according to claim 16 wherein the secondary binding partner is added first and the selective antibody is added subsequently.

32. A method according to claim 1 wherein the secondary binding partner and the selective antibody are added simultaneously.

33. A method according to claim 2 wherein the secondary binding partner and the selective antibody are added simultaneously.

34. A method according to claim 15 wherein the secondary binding partner and the selective antibody are added simultaneously.

35. A method according to claim 16 wherein the secondary binding partner and the selective antibody are added simultaneously.

36. A method according to claim 28 wherein the secondary binding partner is an antibody.

37. A method according to claim 29 wherein the secondary binding partner is an antibody.

38. A method according to claim 30 wherein the secondary binding partner is an antibody.

39. A method according to claim 31 wherein the secondary binding partner is an antibody.

40. A method according to claim 32 wherein the secondary binding partner is an antibody.

41. A method according to claim 33 wherein the secondary binding partner is an antibody.

42. A method according to claim 34 wherein the secondary binding partner is an antibody.

43. A method according to claim 35 wherein the secondary binding partner is an antibody.

44. A method according to claim 28 wherein the secondary binding partner is a monoclonal anti-idiotypic antibody.

45. A method according to claim 29 wherein the secondary binding partner is a monoclonal anti-idiotypic antibody.

46. A method according to claim 30 wherein the secondary binding partner is a monoclonal anti-idiotypic antibody.

47. A method according to claim 31 wherein the secondary binding partner is a monoclonal anti-idiotypic antibody.

48. A method according to claim 32 wherein the secondary binding partner is a monoclonal anti-idiotypic antibody.

49. A method according to claim 33 wherein the secondary binding partner is a monoclonal anti-idiotypic antibody.

50. A method according to claim 34 wherein the secondary binding partner is a monoclonal anti-idiotypic antibody.

51. A method according to claim 35 wherein the secondary binding partner is a monoclonal anti-idiotypic antibody.

52. A method according to claim 3 wherein the primary binding partner is a monoclonal antibody.

53. A kit according to claim 14 wherein the primary binding partner is an immobilized monoclonal antibody.

54. A kit according to claim 27 wherein the primary binding partner is an immobilized monoclonal antibody.

55. A kit according to claim 53 wherein the selective antibody is a labelled monoclonal antibody.

56. A kit according to claim 54 wherein the selective antibody is a labelled monoclonal antibody.

57. A method according to claim 1 wherein the measurement is by electrical or optical means.

58. A method according to claim 15 wherein the measurement is by electrical or optical means.

59. A method according to claim 57 wherein the optical means comprises modification of a surface in which reflectance properties change on deposition.

60. A method according to claim 58 wherein the optical means comprises modification of a surface in which reflectance properties change on deposition.

* * * * *